United States Patent [19]

Cherpeck

[11] Patent Number: 4,584,008
[45] Date of Patent: Apr. 22, 1986

[54] ALDOL ADDUCTS CONTAINING TRIAZOLE GROUPS

[75] Inventor: Richard E. Cherpeck, San Rafael, Calif.

[73] Assignee: Chevron Research Company, San Francisco, Calif.

[21] Appl. No.: 653,749

[22] Filed: Sep. 20, 1984

Related U.S. Application Data

[63] Continuation-in-part of Ser. No. 398,048, Jul. 14, 1982, abandoned.

[51] Int. Cl.$^4$ .................. A01N 43/50; A01N 43/653; C07D 233/60; C07D 249/08
[52] U.S. Cl. .................................. 71/76; 71/92; 514/383; 514/399; 548/262; 548/341
[58] Field of Search .................. 548/262; 514/383; 71/76, 92

[56] References Cited

U.S. PATENT DOCUMENTS

| | | | |
|---|---|---|---|
| 3,658,813 | 4/1972 | Godefrei et al. | 548/341 |
| 3,732,242 | 5/1973 | Buchel et al. | 548/341 |
| 4,079,143 | 3/1978 | Balasubramanyan et al. | 548/262 |
| 4,291,047 | 9/1981 | Kranz et al. | 548/262 |
| 4,315,016 | 2/1982 | Balassubramanyan et al. | 514/383 |
| 4,331,674 | 5/1982 | Kramer et al. | 548/262 |
| 4,366,152 | 12/1982 | Kramer et al. | 548/262 |
| 4,394,380 | 7/1983 | Balasubramanyan et al. | 514/383 |
| 4,517,194 | 5/1985 | Kunz et al. | 548/262 |

FOREIGN PATENT DOCUMENTS

| | | |
|---|---|---|
| 2640823 | 3/1977 | Fed. Rep. of Germany ...... 548/262 |
| 2832234 | 1/1980 | Fed. Rep. of Germany ... 548/262 X |
| 2104065 | 3/1983 | United Kingdom ................ 548/262 |

*Primary Examiner*—Alton D. Rollins
*Attorney, Agent, or Firm*—T. G. DeJonghe; L. S. Squires

[57] ABSTRACT

Compounds of the formula:

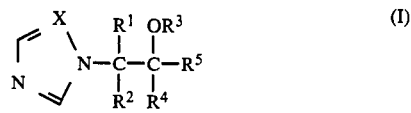

wherein
$R^1$ is cyano, alkoxycarbonyl having 4 through 6 carbon atoms, lower alkylthiocarbonyl, phenoxycarbonyl, halophenoxycarbonyl having from 1 to 3 of the same or different halo ring substituents, N-lower alkylcarbamoyl, N-di(lower alkyl)carbamoyl, phenylmethoxycarbonyl, halophenylmethoxycarbonyl having from 1 to 3 of the same or different halo ring substituents;
$R^2$ is hydrogen or alkyl provided that when $R^1$ is cyano, then $R^2$ is alkyl;
$R^3$ is hydrogen, lower alkanoyl, benzoyl, or halobenzoyl having from 1 through 3 of the same or different halo ring substituents;
$R^4$ is hydrogen, 2-phenylvinyl or 2-halophenylvinyl having 1 through 3 of the same or different halo ring substituents;
$R^5$ is lower alkyl, trihalomethyl, phenyl or substituted phenyl having from 1 through 3 ring substituents independently selected from the group of halo, phenyl, lower alkyl and lower alkoxy; and
X is

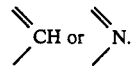

The compounds exhibit fungicidal activity, plant growth regulating activity, and at higher dosages also exhibit herbicidal activity.

21 Claims, No Drawings

ALDOL ADDUCTS CONTAINING TRIAZOLE GROUPS

CROSS REFERENCE TO RELATED APPLICATIONS

This application is a continuation-in-part of U.S. application Ser. No. 398,048 filed July 14, 1982, now abandoned.

BACKGROUND OF THE INVENTION

This invention pertains to novel fungicides, plant growth regulators and herbicides.

Published W. German Patent Application No. DT 2640823 discloses a broad genus of compounds having the general formula:

$$N-N-\underset{\underset{R_1}{\overset{}{\bigwedge}}\underset{N}{\overset{}{\bigwedge}}\underset{R_2}{\overset{}{\bigwedge}}}{\overset{R_3}{\underset{H}{C}}}\left[\underset{H}{\overset{R_4}{\underset{}{C}}}\right]_n OR_5$$

wherein $R_1$ and $R_2$, which may be the same or different, are hydrogen, halogen, nitro or alkyl (e.g., methyl, ethyl, propyl or butyl), $R_3$ is hydrogen, alkoxycarbonyl (e.g., methoxycarbonyl or ethoxycarbonyl) or substituted or unsubstituted hydrocarbyl or hydrocarbyloxy, $R_4$ is phenyl or halogen phenyl, $R_5$ is hydrogen, alkanoyl (e.g., acetyl or propionyl) or substituted or unsubstituted hydrocarbyl; n stands for 0 to 1; $R_5$ is substituted or unsubstituted hydrocarbyl when n is 0, and $R_3$ is something other than substituted or unsubstituted hydrocarbyl when n is 1; and salts thereof. The compounds are described as active fungicides especially against *Piricularia oryzae* on rice; *Puccinia recondita* and other rust diseases on wheat and other host plants; *Plasmapara viticola* on vines; *Erysiphe graminis* (powdery mildew) on barley and wheat and other powdery mildew diseases on various host plants, such as, for instance, *Sphaerotheca fuliginea* on cucumbers, *Podosphaera leucotricha* on apples and *Uncinula necator* on vines; *Botrytis cinerea* (botrytis) on tomatoes, strawberries, vines and other host plants.

U.S. Pat. Nos. 4,315,016 and 4,394,380 claim priority from the same base British applications as W. German Patent Application No. DT 2640823.

U.S. Pat. No. 4,291,047 and German Offenlegungschrift No. 2,832,234 disclose α-azolyl, β-hydroxy ketone derivatives as fungicidal.

U.S. Pat. No. 3,658,813 discloses 1-[β-aryl-β-(R-oxy)-ethyl-imidazoles as fungicidal.

Various imidazole and triazole fungicides are also described in U.S. Pat. Nos. 3,732,242; 4,079,143; 4,315,016; 4,331,674; and 4,366,152.

SUMMARY OF THE INVENTION

The present invention provides compounds and compositions having fungicidal utility. The compounds and compositions are especially effective against the fungal disease powdery mildew and are also significantly effective against the fungal diseases tomato early blight and celery late blight. Two compounds and compositions exhibit plant growth regulating activity and in some instances, at high concentrations exhibit pre-emergence herbicidal activity.

The compounds of the present invention can be represented by the formula:

$$\underset{N}{\overset{X}{\underset{\diagdown}{\bigwedge}}}\underset{}{\overset{}{\diagup}}N-\underset{\underset{R^2}{|}}{\overset{\overset{R^1}{|}}{C}}-\underset{\underset{R^4}{|}}{\overset{\overset{OR^3}{|}}{C}}-R^5 \qquad (I)$$

wherein $R^1$ is cyano, alkoxycarbonyl having 4 through 6 carbon atoms, lower alkylthiocarbonyl, phenoxycarbonyl, halophenoxycarbonyl having from 1 to 3 of the same or different halo ring substituents, N-lower alkylcarbamoyl, N-di(lower alkyl)carbamoyl, phenylmethoxycarbonyl, halophenylmethoxycarbonyl having from 1 to 3 of the same or different halo ring substituents;

$R^2$ is hydrogen or alkyl provided that when $R^1$ is cyano, then $R^2$ is alkyl;

$R^3$ is hydrogen, lower alkanoyl, benzoyl, or halobenzoyl having from 1 through 3 of the same or different halo ring substituents or a compatible cation;

$R^4$ is hydrogen, 2-phenylvinyl or 2-halophenylvinyl having 1 through 3 of the same or different halo ring substituents;

$R^5$ is lower alkyl, trihalomethyl, phenyl or substituted phenyl having from 1 through 3 ring substituents independently selected from the group of halo, phenyl, lower alkyl and lower alkoxy; and X is $$\overset{\diagdown}{\underset{\diagup}{}}CH \text{ or } \overset{\diagdown}{\underset{\diagup}{}}N.$$

Where the particular compound within formula I has an asymmetric carbon atom, the compound may exist as optical isomers. The above formula I is intended to represent both the respective optical isomers and mixtures therof as well as geometric isomers, and such isomers and isomer mixtures are encompassed within the invention.

The invention also provides processes and intermediates for preparing the above compounds.

In a further aspect, the invention provides fungicidal compositions comprising a compatible carrier and an amount of the compound of formula I effective to prevent or arrest the growth of fungi.

In another aspect, the invention provides a method for controlling fungi which comprises applying an amount of the compound of formula I, effective to prevent or arrest the growth of fungi to such fungi or to the potential growth medium of such fungi (e.g., vegetation).

In another aspect, the invention provides a plant growth regulating composition comprising a compatible carrier and an amount of the compound of formula I effective to advantageously alter the growth pattern of such plants.

In still another aspect, the invention provides a method for regulating plant growth which comprises treating the growth medium and/or the foliage of such plants with an amount of the compound of formula I effective to advantageously alter the growth pattern of such plants.

The invention also provides an herbicide composition comprising an herbicidally effective amount of the compound of formula I and a compatible carrier.

The invention also provides a method for preventing or controlling the growth of undesired vegetation which comprises treating the growth medium and/or foliage and/or stems of such vegetation with an herbicidally effective amount of the compound of formula I.

The invention will be further described hereinbelow.

FURTHER DESCRIPTION OF THE INVENTION AND PREFERRED EMBODIMENTS

Illustrations of typical compounds of formula I, of the invention, can be had by reference to Examples 2, 3, 5, 6, 7, 8, and 17 (Table I) set forth hereinbelow on Pages 18–23, and 29.

In part based on their fungicidal properties, the preferred compounds, in terms of their substituents, are those wherein $R^1$ is alkoxycarbonyl, phenylmethoxycarbonyl, halophenylmethoxycarbonyl, phenoxycarbonyl, and halophenoxycarbonyl. The groups isopropoxycarbonyl, t-butoxycarbonyl, neopentoxycarbonyl, 2,4-dihalophenylmethoxycarbonyl (e.g., 2,4-chlorophenylmethoxycarbonyl) are especially preferred, especially t-butoxycarbonyl and neopentoxycarbonyl.

Preferably $R^2$ is hydrogen, methyl or ethyl.

Preferred $R^3$ groups include hydrogen, acetyl, propionyl, benzoyl, halobenzoyl (e.g., 2,4-dichlorobenzoyl).

Preferably $R^4$ is hydrogen.

Preferred $R^5$ groups include trihalomethyl and substituted phenyl, especially trichloromethyl, 4-methoxyphenyl, 4-t-butylphenyl, and 2,4-dichlorophenyl. Preferred dihalophenyls are the 2,4-dihalophenyl. Most preferably, $R^5$ is 2,4-dichlorophenyl.

X is preferably

The preferred compounds are those having one or more of the above preferred substituents and most preferably having a preferred substituent at each respective position. In terms of fungicidal activity the best compounds are those wherein X is nitrogen; $R^1$ is isopropoxycarbonyl and especially t-butoxycarbonyl and neopentoxycarbonyl; $R^2$ is hydrogen or methyl; $R^3$ is hydrogen; $R^4$ is hydrogen and $R^5$ is 2,4-dihalophenyl especially 2,4-dichlorophenyl. This group of compounds is especially effective as preventative fungicides in controlling diseases caused by *Erysiphe polygoni* (e.g., bean powdery mildew); *Septoria apii* (e.g., celery late blight; and *Alternaria solani conidia* (e.g., tomato early blight).

Definitions

As used herein, the following terms have the following meanings, unless expressly stated to the contrary.

The term "alkyl" refers to both straight- and branched-chain alkyl groups. Generally, such alkyl groups contain from 1 through 12 carbon atoms.

The term "lower alkyl" refers to both straight- and branched-chain alkyl groups having from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group $R^6O$- wherein $R^6$ is alkyl.

The term "lower alkoxy" refers to the alkoxy groups having from 1 through 6 carbon atoms and includes, for example, methoxy, ethoxy, t-butoxy, hexoxy, and the like.

The term "lower alkoxycarbonyl" refers to the group

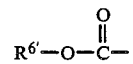

wherein $R^{6'}$ is lower alkyl.

The term "phenoxycarbonyl" refers to the group

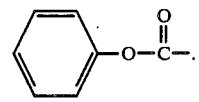

The term "alkylthio" refers to the group having the formula $R^{10}S$- wherein $R^{10}$ is alkyl.

The term "lower alkylthio" refers to such alkylthio groups wherein the alkyl group is a lower alkyl. Typical lower alkyl groups include, for example, methylthio, ethylthio, t-butylthio, and the like.

The term "lower alkanoyl" refers to the group

wherein $R'^6$ is lower alkyl.

The term "2-phenylvinyl" or "styryl" refers to the group

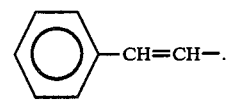

The term "N-lower alkylcarbamoyl" refers to the group

wherein $R'^6$ is lower alkyl.

The term "N-di(lower alkyl)carbamoyl" refers to the group

wherein $R'^6$ and $R'^7$ are independently lower alkyl.

The term "phenylmethoxycarbonyl" or "benzyloxycarbonyl" refers to the group

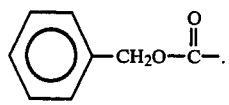

The term "compatible cation" refers to cations which result in salts which do not significantly adversely affect the fungicidal properties of the base compound. Suitable cations include alkali metals (e.g., sodium, potassium, etc.), alkali earth metals; ammonia, and quaternary amine, sulfonium, oxosulfonium salts and the like.

SYNTHESIS

The compounds of the present invention can be conveniently prepared according to the following overall reaction scheme:

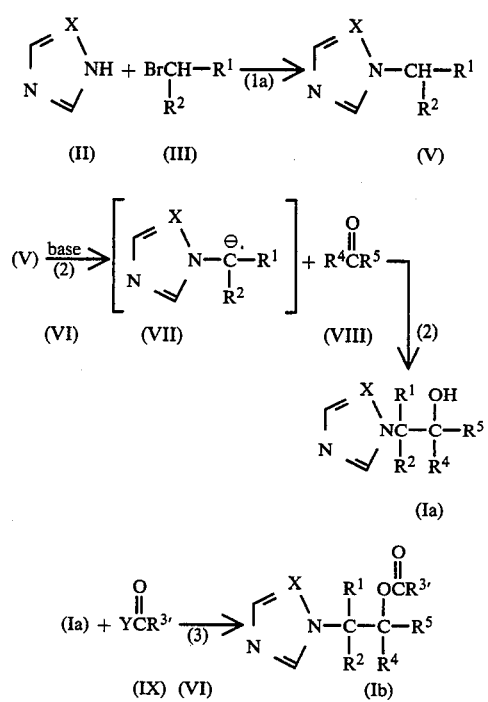

wherein $R^1$, $R^2$, $R^4$, $R^5$, and X are as defined above; Y is a halogen, preferably bromo or chloro; and $R^{3\prime}$ is as defined hereinabove for $R^3$ but is not hydrogen.

Step (1) can be conducted by contacting the appropriate imidazole or triazole II with the appropriate starting material III having the desired $R^1$ and $R^2$ substitution under substantially anhydrous conditions preferably in an inert organic solvent in the presence of a scavenger base. Typically, this process is conducted at temperatures in the range of about from $-20°$ to $80°$ C., preferably $0°$ to $30°$ C., for about from 1 to 72 hours. Generally, about from 0.5 to 5 moles, preferably about from 1 to 1.2 moles, of compound III are used per mole of compound II. Preferably, a base is added to the system to scavenge the acid generated during the reaction. In the case where X is

virtually any base can be used; however, where X is

preferably an amine type base should not be used to avoid conflicting reactions. Suitable bases which can be used include, for example, alkali metal alkoxides, for example, sodium methoxide, and the like.

Suitable inert organic solvents which can be used include, for example, lower alkanols (e.g., methanol, ethanol), tetrahydrofuran, dimethylformamide, dimethyl sulfoxide, and the like and compatible mixtures thereof. Preferably, triazole isomerization is minimized in Reaction (1) by using ethanol as the solvent, sodium ethoxide as the base, and the bromoalkyl reagent, III. The product, IV, can be isolated by suitable procedures such as extraction, filtration, chromatography, distillation or alternatively is used directly in Reaction (2) without purification and/or isolation. The starting materials II and III are generally known compounds and can be prepared by known procedures or by obvious modifications thereof (e.g., substitution of appropriate substituents, solvents, etc.).

It is generally difficult to prepare the intermediates of formula V wherein $R^1$ is alkylthiocarbonyl by the above-described process. Accordingly, it is preferred to prepare these intermediates via the following schematically represented process:

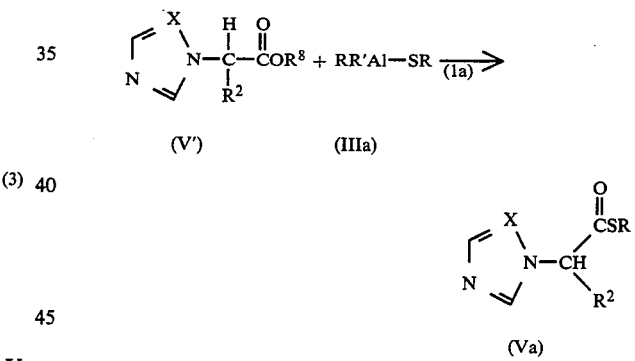

wherein R and $R^8$ are independently lower alkyl; R and R' are independently lower alkyl; and $R^2$ is as defined hereinabove.

Step (1a) can be effected by contacting compound V' with compound IIIa under anhydrous conditions and under an inert atmosphere (e.g., nitrogen, argon, etc.), preferably in an inert organic solvent. Typically, this step is conducted at temperatures in the range of about from $0°$ to $100°$ C., preferably about from $15°$ to $50°$ C., for about from 1 to 24 hours. Generally, about from 0.5 to 2.5 moles, preferably 1.5 to 2 moles, of compound IIIa are used per mole of compound IIa. Suitable inert organic solvents which can be used include, for example, methylene chloride, chloroform, carbon tetrachloride, benzene, toluene, and the like and compatible mixtures thereof.

The compounds of formulas IIIa are known compounds and can be prepared by known procedures, such as for example described in the *Journal of Organic Chemistry*, 42, 3960 (1977), or obvious modifications thereof. The compound of formula IIIa can be conveniently prepared by reacting the desired alkylthiol corresponding to R in formula Va with trialkyl aluminum (e.g., trimethyl aluminum) in an inert organic solvent as described above. Step (1a) can be conveniently conducted in situ by adding IIa to the reaction product mixture.

Step (2) can be effected by contacting intermediate V with compound VIII having the appropriate $R^4$ and $R^5$ substituents in the presence of a base under anhydrous conditions, preferably in an inert organic solvent and under an inert atmosphere. This process is typically conducted at temperatures in the range of about from $-50°$ to 100° C., preferably about from $-50°$ to 0° C., for about from ¼ to 5 hours, using about from 0.5 to 5 moles, preferably 0.9 to 1.2 moles, of compound VIII per compound V. The purpose of the base is to generate the anion of compound V shown as VII in the reaction equation which in turn reacts with compound VIII. Thus, in practice it is preferred to contact compound V with the base prior to the addition of compound VIII. Generally, about from 1 to 3 moles of base are used per mole of compound V and preferably about stoichiometric equivalent amounts of the base (preferably, a base such as lithium diethylamide or lithium diisopropylamide or lithium alkoxides). Other bases which can be used include, for example, alkali metal alkoxides, magnesium amides, and the like.

Suitable inert organic solvents which can be used include, for example, dioxane, tetrahydrofuran, dimethoxyethane, alkyl ethers (e.g., diethyl ether), and the like and compatible mixtures thereof. Preferably, this process is conducted under essentially anhydrous conditions and under an inert atmosphere, conveniently under nitrogen or argon. Also, it is preferred to add the reagents at the lower temperatures within the above temperature range. The reaction is generally complete from within 1 to 24 hours. The product, Ia, can then be isolated by suitable procedures such as, for example, extraction filtration, chromatography, distillation or alternatively, generally can be used directly in Reaction (3) without purification and/or isolation.

Step (3) can be effected by contacting compound Ia with the appropriate acyl halide IX having the desired $R^{3'}$ substituent, under anhydrous conditions preferably in an inert organic solvent in the presence of a scavenger base. Typically, this process is conducted at temperatures in the range of $-20°$ to 100° C., preferably 20° to 100° C., for about from 1 to 24 hours using about from 0.5 to 5 moles, preferably 0.9 to 1.2 moles, of compound IX per mole of compound Ia. Also, since hydrogen halide is generated as a by-product of this reaction, it is preferred to conduct this process in the presence of a scavenger base to react with the by-product as it is generated. Suitable bases which can be used include, for example, pyridine, triethylamine, 4-dimethylaminopyridine, and the like.

Suitable inert organic solvents which can be used include, for example, chloroform, methylene chloride, toluene, benzene, and the like. The product, Ib, is then isolated by conventional procedures such as extraction, filtration, chromatography, distillation, and the like.

The salts of formula I (i.e., $R^3$ is a cation) can be prepared by reacting the corresponding hydroxy compound of formula I ($R^3$ is H) with a strong base such as metal hydrides and metal alkoxides via conventional procedures. For example by reaction of a compound of formula I ($R^3$ is H) with sodium methoxide in an appropriate alcoholic solvent to prevent ester exchange. It is also noted that in water solutions many of the salts are unstable and in water will spontaneously convert back to the hydroxy compound. Additional variation in the cation can be effected by contacting the sodium salt or potassium salt with a cation exchange resin having the desired cation.

Generally, the reactions described above are conducted as liquid-phase reactions and hence pressure is generally not significant except as it affects temperature (boiling point) where reactions are conducted at reflux. Therefore, these reactions are generally conducted at pressures of from 300 to 3000 mm mercury and conveniently are conducted at about atmospheric or ambient pressure.

It should also be appreciated that where typical or preferred process conditions (e.g., reaction temperatures, times, mole ratios of reactants, solvents, etc.) have been given, that conditions above or below these ranges may also be used in some instances but generally with poorer results or economies. Optimum conditions may vary with the particular reagents or organic solvents used but can be determined by routine optimization procedures.

Where optical isomer mixtures are obtained, the respective optical isomers can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts.

Utility

The compounds of the present invention are effective in controlling fungal infections especially when applied as preventative fungicides. The compounds of the invention are particularly effective against powdery mildew fungal infections caused by such organisms as *Erysiphe polygoni*. Certain of the compounds of this invention are also useful in controlling leaf blights caused by organisms such as *Septoria apii*, and *Alternaria solani conidia* and/or controlling fungal infections caused by *Plasmopara viticola*, *Uromyces phaseoli tipica*, and *Piricularia oryzae*. Tables VI and VII list a summary of activity against some particular fungi for several compounds of this invention.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.05% to 95% of the toxicant by weight of the fungicidal composition, and depending on whether the composition is intended for direct application or dilution prior to application. The compounds are typically applied at rates in the range of about from 0.1 to 5 kg/hectare, preferably 0.2 to 3 kg/hectare, and typically are applied as foliage sprays.

The fungicidal compositions may be formulated and applied with other active ingredients, including other fungicides, insecticides, nematocides, bactericides, plant growth regulators, fertilizers, etc. At higher concentrations, the compounds of the invention also exhibit modest pre-emergent and post-emergent herbicidal activity against a variety of broadleaved weeds, including Mustard, Pigweed, and Lambsquarter. At relatively high concentrations, the compounds also have pre-emergent herbicidal activity against a variety of grasses. Thus, the compounds can be applied as herbicides either directly or more pragmatically can be applied in an herbicidal composition comprising the active compound in an inert carrier or diluent.

Such herbicidal compositions comprise from about 5% to 95% by weight of the herbicidal compounds of the invention, intimately admixed with a biologically inert liquid or solid carrier, e.g., powders, dusts or granules. Suitable liquid diluents which can be used include, for example, water, organic solvents (e.g., hydrocarbons such as benzene, toluene, kerosene, diesel fuel, fuel oil, petroleum naphtha, etc.), and the like. Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials such as, for example, walnut shell flour, cottonseed hulls, wheat flour, wood flour, wood bark flour, and the like can also be used as carriers. The herbicidal composition typically also contains a small amount of one or more surface-active agents such as wetting agents and dispersing agents and can also contain compatible insecticides and additional compatible herbicides. The surface-active agent can either be anion, cationic or nonionic in character. The herbicidal composition can also contain compatible pesticides and adjuvants, stabilizers, conditioners, fillers, and if desired, other herbicidally active compounds, and the like.

The herbicidal compounds or the herbicidal compositions of the invention can be applied by conventional procedures which are well known by the art. For example, where the herbicide is applied in a pre-emergent application, it is applied directly to the area of soil desired to be protected. For post-emergent application, the herbicidal compositions will be applied directly to the foliage or other plant parts. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for pre-emergent control, the herbicidal compounds are applied at rates of about from 5 to 60 kg/ha. For post-emergent control, higher dosages in the range of about from 10 to 60 kg/ha are typically used.

More significantly, the compounds also exhibit plant growth regulating activity, including general yield enhancement and also stunting activity against grass crops. This stunting activity is particularly desirable in the case of crops such as wheat, since it reduces matting caused by the tall stems intertwining, without adversely affecting the amount of grain yielded, and in some instances even improves the yield.

The present compounds of formula I can be applied in pure form, but more pragmatically, as in the case of herbicide application, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and selective herbicides. Typically, the plant growth regulating composition will contain a total of about from 0.1 to 95 weight percent, of one or more compounds of formula I, depending on whether the composition is designed for direct use or dilution prior to application. Generally, for plant growth regulating activity, the compounds of formula I will be applied at a dosage of about from 1 to 10 kg/ha, depending on the mode of application, plant, and type of plant growth regulating effect desired. The compounds are preferably applied as a seed pretreatment or soil drench as the compounds are best absorbed through the roots of the plant. As a seed pretreatment for yield enhancement, the compounds are generally preferably applied at a dosage of about 2 to 16 gms per 100 kg of seeds. As a soil drench, the compounds are generally preferably applied at a rate of about from 1 to 2.5 kg/hectare. At these soil drench rates, the compounds are generally ineffective as foliage sprays.

A further understanding of the invention can be had in the following non-limiting Examples. Wherein, unless expressly stated to the contrary, all temperatures and temperature ranges refer to the centigrade system and the term "ambient" or "room temperature" refers to about 20° to 25° C. The term "percent" refers to weight percent and the term "mole" or "moles" refers to gram moles. The term "equivalent" refers to a reagent equal in moles, to the moles of the proceding or succeeding reactant recited in that example in terms of finite moles or finite weight or volume. Unless expressly stated to the contrary, E and Z isomers are generated where appropriate and are not separated. Also, unless expressly stated to the contrary, geometric isomer and racemic mixtures are used as starting materials and correspondingly isomer mixtures are obtained as products.

EXAMPLES

Example 1 t-butyl-α-(1,2,4-triazol-1-yl)acetate

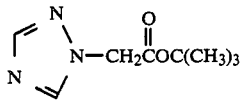

34.53 gms of 1,2,4-triazole were added to 250 mls of ethanol along with 34.0 gms of sodium ethoxide. The system was placed under an argon atmosphere and cooled to about 0° C. After cooling, 107.28 gms of t-butyl bromoacetate were dropwise added to the system. The system was then allowed to come to room temperature and stirred there for 60 hours. The reaction was stopped and the system filtered. The solvent was removed by stripping and the residue was dissolved in hot ether and then filtered. The ether was removed by stripping and the resulting solid triturated with hexane and dried to yield 80.81 gms of the title compound as a beige solid.

Example 1a 1-cyano-1-(1,2,4-triazol-1-yl)ethane

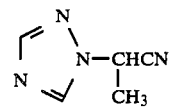

In this example, a mixture containing 13.47 gms (0.195 mole) of 1,2,4-triazole and 10.53 gms (0.195 mole) of sodium methoxide in 200 mls of dimethylformamide was refluxed until no further evolution of the methanol by-product was observed. The reaction mixture was then cooled to 0° C. and then 19.23 gms of 2-chloropropionitrile dissolved in 25 mls of dimethylformamide were added dropwise with stirring. The mixture was then stirred overnight (about 12 to 14 hours) at room temperature and then filtered. The dimethylformamide was then removed by vacuum evaporation. The residue was dissolved in methylene chloride and filtered through neutralized silica gel. The filtrate was evaporated affording 16.73 gms of the title compound as a brown liquid.

Similarly, by following the same procedure but using 1,3-diazole in place of 1,2,4-triazole, 1-cyano-1-(1,3-diazol-1-yl)ethane can be prepared.

Example 1b t-butyl-α-(1,2,4-triazol-1-yl)thioacetate

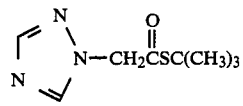

In this example, 18 mls (0.16 mole) of t-butylthiol was added dropwise to 80 mls of a mixture containing 0.16 mole of trimethyl aluminum in methylene chloride at room temperature. The resulting mixture was allowed to warm to room temperature and stirred for 15 minutes. 12.4 gms (0.08 mole) of ethyl α-(1,2,4-triazol-1-yl)acetate in 40 mls of methylene chloride was then added dropwise and the mixture stirred for 22 hours at room temperature. The mixture was then cooled to 0° C. and quenched by the slow addition of aqueous 3 wt. % hydrochloric acid. The resulting aqueous layer was extracted three times with methylene chloride. The combined extracts were washed twice with aqueous 5 wt. % sodium hydroxide, then washed with water and dried over sodium sulfate. The mixture was then evaporated under vacuum affording 5 gms of the title compound as a white solid.

Similarly, by following the same procedure but using ethyl α-(1,3-imidazol-1-yl)acetate in place of the triazole ester, t-butyl α-(1,3-imidazol-1-yl)thioacetate can be prepared.

Example 2 t-butyl-α-(1,2,4-triazol-1-yl)-β-hydroxy-β-(2,4-dichlorophenyl)propionate

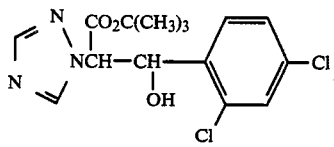

In this example 1.0 of sodium methoxide was slowly added portionwise, under nitrogen, to a mixture containing 3.0 g of t-butyl 1-triazoyl acetate; 2.86 g of 2,4-dichlorobenzaldehyde and 0.7 g of lithium bromide in 40 ml of anhydrous tetrahydrofuran at 0° to 5° C. The mixture was stirred for one hour at 0° C. and then quenched by the addition of 10 ml of saturated aqueous ammonium chloride solution. Ten ml of water was added and the mixture then extracted with 25 ml of ethyl acetate. The ethyl acetate extract was evaporated to dryness. The residue was washed and evaporated three times with toluene. Additional toluene was added and the resulting slurry was filtered. The filter cake was washed with toluene and then subjected to high vacuum evaporation affording 4.5 g of the title compounds as the residue.

Example 3

1-cyano-1-methyl-1-(1,2,4-triazol-1-yl)-2-hydroxy-2-(2,4-dichlorophenyl)ethane

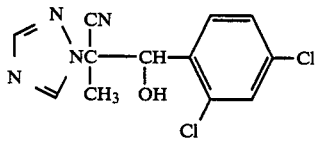

To a 3-neck, 250-ml flask equipped with an addition funnel, argon inlet and a septum were added 25 mls of anhydrous tetrahydrofuran and 5.7 mls of diisopropylamine (passed through activity I neutral alumina) under an argon atmosphere. The system was cooled to about 0° C. and 33 mls of 1.6M butyl lithium solution (in hexane) were then added via a syringe. The system was stirred at 0° C. for 5 minutes and then further cooled to −68° C. After cooling, 6.1 gms of 1-cyano-1-(1,2,4-triazol-1-yl)ethane in tetrahydrofuran were added to the system. The system was stirred at −68° C. for 1 hour and then 8.8 gms of 2,4-dichlorobenzaldehyde were slowly added to the system. The system was allowed to warm to room temperature over 30 minutes. Saturated aqueous ammonium chloride was then added to the system and the product was extracted with methylene chloride. The organic solution was washed with water, dried over sodium sulfate and filtered. The solvent was removed by stripping to yield a yellow oil. This oil was then taken up in diethyl ether resulting in the precipitation of 4.1 gms of the erythio isomer of the title compound. The mother liquors were concentrated and again taken up in diethyl ether resulting in the precipitation of 2.60 gms of the threo isomer of the title compound, m.p. 164°–168° C.

Example 4 t-butyl-α-imidazol-1-yl acetate 6.13 gms of imidazole were added to 50 mls of dichloromethane. After addition, the system was cooled to 0° to 5° C. 4.3 gms of tert-butyl chloroacetate in 25 mls of methylene chloride were added to the system. The system was then allowed to come to room temperature and stirred there for 16 hours. The system was then heated to reflux for an additional 16 hours. The organic solution was then washed with water, dried over anhydrous sodium sulfate and filtered. The solvent was removed by stripping to yield 4.12 gms of the title compound, m.p., 104°–107° C.

Example 5 t-butyl-α-(imidazol-1-yl)-β-hydroxy-β-(2,4-dichlorophenyl)propionate

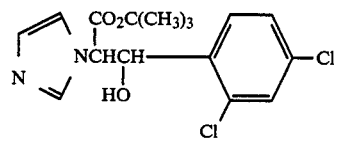

To a 3-neck, 250-ml flask equipped with an addition funnel, argon inlet and a septum were added 20 mls of anhydrous tetrahydrofuran and 2.5 mls of diisopropylamine (passed through activity I neutral alumina) under an argon atmosphere. The system was cooled to about 0° C. and 10.3 mls of 1.6M butyl lithium solution (in hexane) were then added via a syringe. The system was stirred at 0° C. for 5 minutes and then further cooled to −68° C. After cooling, 2.73 gms (0.015 mole) of t-butyl α-(1,2,4-imidazol-1-yl)acetate in tetrahydrofuran were added to the system. The system was stirred at −68° C. for 1 hour and then 2.63 gms of 2,4-dichlorobenzaldehyde were slowly added to the system. The system was stirred at −68° C. for an additional 10 minutes and then was allowed to warm to room temperature over 45 minutes. Saturated aqueous ammonium chloride was then added to the system and the product was extracted with methylene chloride. The organic solution was washed with water, dried over sodium sulfate and filtered. The solvent was removed by stripping to yield a yellow oil. The oil was taken up in diethyl ether and the title compound precipitated out and was recovered; 1.57 gms, m.p., 149°–157° C.

Example 6 t-butyl-2-(imidazo-1-yl)-3-hydroxy-3,5-di-(4-chlorophenyl)pent-4-enoate

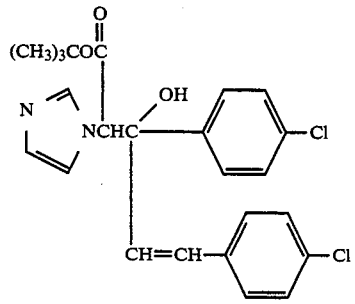

To a 3-neck, 250-ml flask equipped with an addition funnel, argon inlet and a septum were added 20 mls of anhydrous tetrahydrofuran and 2.5 mls of diethylamine (passed through activity I neutral alumina) under an argon atmosphere. The system was cooled to about 0° C. and 14.2 mls of 1.6M butyl lithium solution (in hexane) were then added via a syringe. The system was stirred at 0° C. for 5 minutes and then further cooled to −68° C. After cooling, 3.64 gms of t-butyl α-(imidazol-1-yl)acetate in tetrahydrofuran were added to the system. The system was stirred at −68° C. for 1 hour and then 5.54 gms of 4-chlorophenyl 2-(4-chlorophenyl)vinyl ketone were slowly added to the system. The system was stirred at −68° C. for an additional 5 minutes and then was allowed to warm to room temperature over 45 minutes. Saturated aqueous ammonium chloride was then added to the system and the product was extracted with methylene chloride. The organic solution was washed with water, dried over sodium sulfate and filtered. The solvent was removed by stripping to yield 8.88 gms of an oily solid. This solid was triturated with diethyl ether affording 4.4 gms of the title compound, m.p., 72°–80° C.

Example 7 t-butyl-α-(1,2,4-triazol-1-yl)-β-propionoxy-β-(2,4-dichlorophenyl)propionate

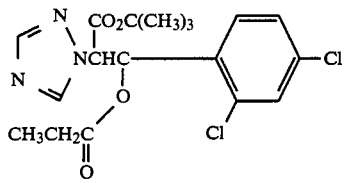

3.15 gms of t-butyl α-(1,2,4-triazol-1-yl)-β-hydroxy-β-(2,4-dichlorophenyl)propionate were added to 50 mls of chloroform along with 1.1 gms of 4-dimethylaminopyridine. 1.25 gms of propionyl chloride were then added to the system. The reaction mixture was then refluxed for 18 hours. The reaction solution was then first washed with aqueous 5 wt. % hydrochloric acid and then with aqueous sodium hydroxide. The organic phase was dried over sodium sulfate and then filtered. The filtrate was evaporated to dryness under vacuum affording 2.78 gms of the title compound as a yellow wax.

Example 8

By following the appropriate procedures set forth in the above examples but using the appropriately substituted starting materials, the compounds listed in Table I of Example 17, set forth hereinbelow, were respectively prepared.

Similarly, by following the appropriate procedures set forth in the above examples and appropriately substituted starting materials, the following compounds can also be prepared:

phenyl-α-(1,2,4-triazol-1-yl)-β-hydroxy-β-(2,4-dichlorophenyl)propionate;
hexyl-α-(1,2,4-triazol-1-yl)-β-hydroxy-β-(2,4-difluorophenyl)propionate;
ethyl-α-(1,2,4-triazol-1-yl)-β-hydroxy-β-(2,3,4-tribromophenyl)propionate;
methy-α-(1,2,4-triazol-1-yl)-β-benzoyloxy-β-(2-chloro-4-fluorophenyl)propionate;
t-butyl-α-propyl-(1,2,4-triazol-1-yl)-β-acetoxy-β-(2,6-dimethylphenyl)propionate;
ethyl-α-t-butyl-(1,2,4-triazol-1-yl)-β-4-fluorobenzoyloxy-β-phenylvinyl-β-hexylpropioniate;
1-t-butylcarbamoyl-1-(1,2,4-triazol-1-yl)-2-hydroxy-2-phenylethane;
t-butyl-2-(1,2,4-triazolyl-1-yl)-3-hydroxy-3-(4-chlorophenyl)-5-phenyl-pent-4-enoate;
t-butyl-α-(imidazo-1-yl)-β-hydroxy-β-(2,4-dichlorophenyl)propionate;
1-cyano-1-methyl-1-(imidazo-1-yl)-2-acetoxy-2-(2,6-dimethylphenyl)ethane;
t-butyl-α-(imidazo-1-yl)-β-hydroxy-β-(4-methoxyphenyl)propionate;
phenyl-α-(imidazo-1-yl)-β-hydroxy-β-(2,4-dichlorophenyl)propionate;
hexyl-α-(imidazol-1-yl)-β-hydroxy-β-(2,4-difluorophenyl)propionate;
ethyl-α-(imidazo-1-yl)-β-hydroxy-β-(2,3,4-tribromophenyl)propionate;
methyl-α-(imidazo-1-yl)-β-benzoyloxy-β-(2-chloro-4-fluorophenyl)propionate;
t-butyl-α-propyl-(imidazo-1-yl)-β-acetoxy-β-(2,6-dimethylphenyl)propionate;
ethyl-α-t-butyl-(imidazo-1-yl)-β-4-fluorobenzoyloxy-β-phenylvinyl-β-hexylpropionate;
1-t-butylcarbamoyl-1-(imidazo-1-yl)-2-hydroxy-2-phenylethane; and
t-butyl-2-(1,2,4-imidazo-1-yl)-3-hydroxy-3-(4-chlorophenyl)-5-phenyl-pent-4-enoate.

Example 9

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° to 80° F.; relative humidity was maintained at 40% to 60%. Two replicates (plants) are used for each compound and the check. The percent disease control provided by a given test compound was based on the percent disease reduction relative to the untreated check plants. The averaged results are tabulated in Table IV.

Example 10

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° to 68° F. and 100% relative humidity for at least 16 hours. Following the incubation, the plants were maintained in a greenhouse for approximately 7 days. Two replicates (plants) are used for each compound and the check. The percent disease control provided by a given test compound was based on the percent disease reduction relative to untreated check plants. The averaged results are tabulated in Table IV.

Example 11

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° to 68° F. in 100% relative humidity for an extended period of time (approximately 48 hours). Following the incubation, the plants were allowed to dry and then were maintained in a greenhouse for approximately 14 days. Two replicates (i.e., plants) were used for each compound and the check. The percent disease control provided by a given candidate toxicant is based on the percent disease reduction relative to untreated check plants. The averaged results are reported in Table IV.

Example 12

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in an environmental chamber and incubated at 66° to 68° F. and 100% relative humidity for 24 hours. Following the incubation, the plants were maintained in a greenhouse for about 12 days. Percent disease control was based on the percent disease development on untreated check plants. Two replicates (plants) were used for each compound and the check. The compounds tested and the averaged results are tabulated in Table IV.

Example 13

Grape Downy Mildew

The compounds of the invention were tested for the control of the Grape Downy Mildew organism *Plasmopara viticola*. About 7-week-old *Vitis vinifera* cultivar Emperor grape seedlings were used as hosts. The plants were sprayed with a 250-ppm solution of the test compound in acetone. The sprayed leaves were dried, inoculated with a spore suspension of the organism, placed in a humid environmental chamber and incubated at 66° to 68° F. and about 100% relative humidity. After incubation for 2 days, the plants were then held in a greenhouse 7 to 9 days; then the amount of disease control was determined. Two plants were used for each compound and the check. The percent disease control provided by a given test compound was based on the percent disease reduction relative to untreated check plants. The results are tabulated in Table IV.

Example 14

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table IV.

Example 15

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants.

$$\% \text{ Control} = 100 \times \left( \frac{\% \text{ disease in treated plants}}{\% \text{ disease in check}} \right)$$

The results are tabulated in Table IV.

Example 16

Pre-emergent Herbicidal Test

The test solution was prepared as follows: 355.5 mgs of test compound were dissolved in 15 mls of acetone. Two mls of acetone containing 110 mgs of a nonionic surfactant were added to the solution. Twelve mls of this stock solution were then added to 47.7 mls of water which contained the same nonionic surfactant at a concentration of 625 mgs/l.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity and 100 representing complete kill. The results of these tests appear in Table V.

Example 17

Post-emergent Herbicidal Test

The test compound was formulated in the same manner as described above for the pre-emergent test. This formulation was uniformly sprayed on 2 similar pots containing plants 2 to 3 inches tall (except Wild Oats, Soybean and Watergrass which were 3 to 4 inches tall) (approximately 15 to 25 plants per pot) at a dose of 27.5 micrograms/cm². After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests appear Table V.

TABLE I

Compounds of the Fromula:

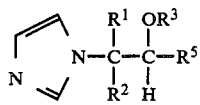

| Compound No. | R¹ | R² | R³ | R⁵ | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 1 | —COC(CH₃)₃ (C=O) | H | H | 3,4-Cl₂-C₆H₃ | 53.79 | 54.36 | 5.08 | 5.70 | 7.84 | 8.08 | white solid | 149°–157° C. |
| 2 | —CN(CH₃)₂ (C=O) | H | H | 3,4-Cl₂-C₆H₃ | 51.23 | 54.52 | 4.61 | 5.18 | 12.80 | 15.82 | white solid | 161°–166° C. |

TABLE II

Compounds of the Formula:

$$\begin{array}{c} N \\ \parallel \\ N \end{array} N - \underset{R^2}{\overset{R^1}{\underset{|}{C}}} - \underset{H}{\overset{OR^3}{\underset{|}{C}}} - R^5$$

| Compound No. | R¹ | R² | R³ | R⁵ | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 3 | −COC(CH₃)₃ (C=O) | H | H | 2,4-dichlorophenyl | 50.29 | 50.70 | 4.78 | 5.10 | 11.73 | 12.12 | white solid | 177°−185° C. |
| 4 | −COC(CH₃)₃ (C=O) | H | −C(=O)−phenyl | 2,4-dichlorophenyl | 57.15 | 54.12 | 4.58 | 4.84 | 9.09 | 11.87 | white solid | 105°−107° C. |
| 5 | −COC(CH₃)₃ (C=O) | H | −C(=O)CH₂CH₃ | 2,4-dichlorophenyl | 52.18 | 47.72 | 5.11 | 4.69 | 10.14 | 9.92 | yellow waxy solid | — |
| 6 | −COCH(CH₃)CH₃ (C=O) | −CH₃ | H | 2,4-dichlorophenyl | 48.57 | 50.11 | 4.95 | 4.89 | 12.14 | 12.28 | white solid | 138°−142° C. |
| 7 | −COC₂H₅ (C=O, ester) | −CH₃ | H | 2,4-dichlorophenyl | 48.85 | 50.13 | 4.37 | 4.76 | 12.21 | 12.83 | white solid | 164°−168° C. |
| 8 | −CN | −CH₃ | −C(=O)−phenyl | 2,4-dichlorophenyl | 56.87 | 57.20 | 3.52 | 3.50 | 13.96 | 13.41 | yellow foam | — |

TABLE II-continued

Compounds of the Formula:

$$\begin{array}{c} N{\equiv}\!\!\!\!\diagdown \\ \phantom{N}\diagup N{-}\underset{R^2}{\overset{R^1}{\underset{|}{C}}}{-}\underset{H}{\overset{OR^3}{\underset{|}{C}}}{-}R^5 \end{array}$$

| Compound No. | R¹ | R² | R³ | R⁵ | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 9 | —CO(CH₃)₃ (O=) | H | H | 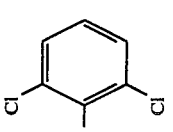 2,6-diCl-phenyl-CH₃ | 50.29 | 52.40 | 4.78 | 5.12 | 11.73 | 13.25 | white solid | 128°–131° C. |
| 10 | —COCH₂—(2,4-diCl-phenyl) (O=) | H | H | 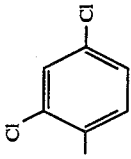 2,4-diCl-phenyl-CH₃ | 46.88 | 47.57 | 2.84 | 3.28 | 9.11 | 9.89 | white solid | 178°–180° C. |
| 11 | —CN (threo) | —CH₃ | H | 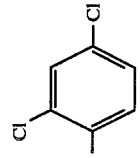 2,4-diCl-phenyl-CH₃ | 48.50 | 49.20 | 3.39 | 3.66 | 18.86 | 20.32 | white solid | 164°–168° C. |
| 12 | —CN (erytho) | —CH₃ | H | 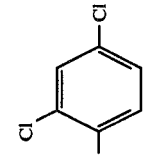 2,4-diCl-phenyl-CH₃ | 48.50 | 51.25 | 3.39 | 3.59 | 18.86 | 21.08 | white solid | 194°–196° C. |
| 13 | —COC(CH₃)₃ (O=) | H | H | —CCl₃ | 36.33 | 38.49 | 4.27 | 4.40 | 12.71 | 14.14 | beige solid | 178°–180° C. |
| 14 | —CN(CH₃)₂ (O=) | H | H | 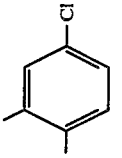 2,4-diCl-phenyl-CH₃ | 47.73 | 50.63 | 4.29 | 4.58 | 17.02 | 18.66 | beige solid | 161°–166° C. |

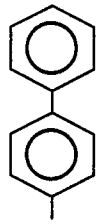

TABLE II-continued

Compounds of the Formula:

$$\underset{N}{\underset{\|}{N}}\!\!\diagdown\!\!N\!-\!\underset{R^2}{\overset{R^1}{\underset{|}{C}}}\!-\!\underset{H}{\overset{OR^3}{\underset{|}{C}}}\!-\!R^5$$

| Compound No. | R[1] | R[2] | R[3] | R[5] | Carbon Calc. | Carbon Found | Hydrogen Calc. | Hydrogen Found | Nitrogen Calc. | Nitrogen Found | Form | m.p. |
|---|---|---|---|---|---|---|---|---|---|---|---|---|
| 21 | O=\|−COCH(CH₃)₂ | H | H | −C₆H₅ (phenyl) | 62.05 | 61.88 | 6.94 | 6.78 | 14.47 | 15.86 | white solid | 168°–171° C. |
| 22 | O=\|−COC(CH₃)₃ | H | H | −CH(CH₃)₂ | 56.45 | 56.18 | 8.29 | 8.54 | 16.46 | 13.24 | white solid | 126°–128° C. |
| 23 | O=\|−COC(CH₃)₃ | H | H | 4-OCH₃-C₆H₄ | 60.17 | 62.62 | 6.60 | 6.98 | 13.15 | 14.72 | white solid | 128°–131° C. |
| 24 | O=\|−COCH₂C(CH₃)₃ | H | H | 2,4-diCl-C₆H₃ | 51.62 | 52.19 | 5.14 | 5.65 | 11.29 | 10.82 | white solid | 179°–181° C. |
| 25 | O=\|−COCH(CH₃)₂ | H | H | 2,4-diCl-C₆H₃ | 48.85 | 47.39 | 4.39 | 4.68 | 12.21 | 12.01 | white solid | 196°–201° C. |
| C-1* | O=\|−COCH₂CH₃ | H | H | 2,4-diCl-C₆H₃ | 49.70 | 48.14 | 4.17 | 4.14 | 13.38 | 12.72 | white solid | 198°–199° C. |

*Comparison Compound disclosed in laid open W. German Application DT 2640823

TABLE III

| Compound No. | COMPOUND | ANALYSIS Carbon Calc. | Found | Hydrogen Calc. | Found | Nitrogen Calc. | Found | Form | m.p. |
|---|---|---|---|---|---|---|---|---|---|
| 26 | 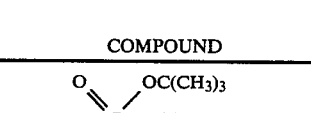 | 62.75 | 60.02 | 5.27 | 5.42 | 6.10 | 6.01 | white solid | 72°–80° C. |

TABLE IV

Fungicidal Activity
% Control

| Compound No. | GDM | TLB | CLB | TEB | BR | BPM | RB |
|---|---|---|---|---|---|---|---|
| 1 | 10 | 0 | 17 | 27 | 50 | 93 | 0 |
| 2 | 6 | 22 | 47 | 5 | 0 | 63 | 0 |
| 3 | 0 | 8 | 100 | 98 | 46 | 100 | 0 |
| 4 | 0 | 24 | 91 | 78 | — | 100 | 13 |
| 5 | 0 | 0 | 96 | 52 | 4 | 100 | 27 |
| 6 | 15 | 4 | 92 | 25 | 43 | 100 | 0 |
| 7 | 16 | 0 | 0 | 25 | 0 | 100 | — |
| 8 | 13 | 17 | 0 | 8 | 0 | 100 | 65 |
| 9 | 0 | 0 | 3 | — | — | 100 | 0 |
| 10 | 3 | 23 | 96 | 27 | 0 | 100 | 42 |
| 11 | 0 | 36 | 50 | 0 | 0 | 100 | 96 |
| 12 | 0 | 0 | — | 0 | 16 | 100 | 52 |
| 13 | 0 | 0 | — | 27 | 75 | 100 | 29 |
| 14 | 10 | 0 | 7 | 29 | 0 | 100 | 0 |
| 15 | 63 | 0 | 0 | 14 | 0 | 100 | 0 |
| 16 | 0 | 0 | — | 0 | 0 | 0 | 4 |
| 17 | 0 | 4 | — | 0 | 0 | 0 | 33 |
| 18 | 17 | 0 | 64 | 0 | 4 | 100 | 25 |
| 19 | 0 | 0 | 0 | 57 | 33 | 100 | 21 |
| 20 | 30 | 0 | 20 | 27 | 0 | 100 | — |
| 21 | 3 | 0 | 60 | 7 | 0 | 100 | 0 |
| 22 | 3 | 0 | 0 | 0 | 0 | 56 | 0 |
| 23 | 3 | 0 | 70 | 7 | 20 | 100 | 0 |
| 24 | 0 | 0 | 94 | 60 | 13 | 100 | 25 |
| 25 | — | 0 | 38 | 75 | 0 | 100 | 0 |
| 26 | 65 | 61 | 0 | 44 | — | 85 | 13 |
| C-1 | 0 | 0 | 21 | 0 | 0 | 100 | 0 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani condia*)
BR - Bean Rust (*Uromyces phaseoli tipica*)
BPM - Bean Powdery Mildew (*Erysiphe polygoni*)
RB - Rice Blast (*Piricularia oryzae*)
— not tested

TABLE V

Herbicidal Activity
% Control
Pre/Post

| Compound No. | Lambs-quarter | Mustard | Pigweed | Crabgrass | Watergrass | Wild Oats |
|---|---|---|---|---|---|---|
| 1 | 65/0 | 30/0 | 63/0 | 0/0 | 0/0 | 0/0 |
| 3 | 100/15 | 70/0 | 85/50 | 0/0 | 0/0 | 0/0 |
| 4 | 99/40 | 50/45 | 80/68 | 35/0 | 0/0 | 0/0 |
| 5 | 100/0 | 62/30 | 90/60 | 0/0 | 0/0 | 0/0 |
| 6 | 95/50 | 95/50 | 90/50 | 90/0 | 50/0 | 0/0 |
| 7 | 90/30 | 58/45 | 80/35 | 45/0 | 40/0 | 35/0 |
| 8 | 70/30 | 30/0 | 85/0 | 50/0 | 0/0 | 0/0 |
| 11 | 100/0 | 99/0 | 95/0 | 15/0 | 15/0 | 15/0 |
| 12 | 99/0 | 45/0 | 80/0 | 25/0 | 45/0 | 0/0 |
| 24 | 80/0 | 55/0 | 45/0 | 0/0 | 0/0 | 0/0 |
| 25 | 90/30 | 58/45 | 80/35 | 45/0 | 40/0 | 35/0 |
| 26 | 100/0 | 60/0 | 80/0 | 0/0 | 0/0 | 0/0 |

Compound Nos. 2, 9, 10, 13–23 and 27 did not show any significant herbicide activity in this test.

Example 18

In this example compounds numbers 3, 6, 25 and C-1 were tested at lower dosages for preventative fungicidal activity with respect to bean powdery mildew (*Erysiphe polygoni*); celery late blight (*Septoria apii*) and tomato early blight (*Alternaria solani conidia*). In these tests all four compounds were tested side by side. The tests were conducted in the same manner as described hereinabove in Examples 9, 11 and 12, respectively, with the exception that the dosages indicated in Tables VI–VIII hereinbelow were used and four replicates (i.e., plants) were used for each compound. The average results are reported in Tables VI, VII and VIII hereinbelow. (For convenience of reference numbers 3, 6, 25 and C-1 are identified in Table A below.)

TABLE A

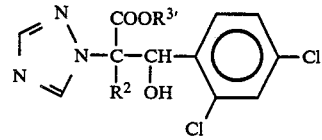

| Compound No. | $R^2$ | $R^{3'}$ |
|---|---|---|
| C-1 | H | —CH$_2$CH$_3$ |
| 3 | H | —C(CH$_3$)$_3$ |
| 6 | CH$_3$ | —CH(CH$_3$)$_2$ |
| 25 | H | —CH(CH$_3$)$_2$ |

TABLE VI

Preventative Activity - Celery Late Blight
Percent Control

| Dosage ppm | Compound C-1 | Compound 3 | Compound 6 | Compound 25 |
|---|---|---|---|---|
| 200 | 10 | 76 | 72 | 66 |
| 80 | 3 | 66 | 67 | 60 |
| 32 | 3 | 34 | 34 | 60 |

TABLE VI-continued

| | Preventative Activity - Celery Late Blight | | | |
|---|---|---|---|---|
| | Percent Control | | | |
| Dosage ppm | Compound C-1 | Compound 3 | Compound 6 | Compound 25 |
| *ED 50/90 | **N.C. | 56/388 | 58/430 | **N.C. |

Percent Infection in Check Plants: 73%
*ED 50/90: Effective Dosage 50% control and 90% control, respectively, in parts per million (ppm)
**N.C.: Not Calculated

TABLE VII

| | Preventative Activity - Tomato Early Blight | | | |
|---|---|---|---|---|
| | Percent Control | | | |
| Dosage ppm | Compound C-1 | Compound 3 | Compound 6 | Compound 25 |
| 200 | 23 | 89 | 57 | 71 |
| 80 | 40 | 69 | 34 | 46 |
| 32 | 29 | 66 | 60 | 17 |
| ED 50/90 | N.C. | 21/228 | N.C. | 98/450 |

Percent Infection in Check Plants: 44%

TABLE VIII

| | Preventative Activity - Bean Powdery Mildew | | | |
|---|---|---|---|---|
| | Percent Control | | | |
| Dosage ppm | Compound C-1 | Compound 3 | Compound 6 | Compound 25 |
| 0.32 | 43 | 96 | 85 | 89 |
| 0.13 | 15 | 85 | 65 | 54 |
| 0.05 | 19 | 81 | 33 | 56 |
| ED 50/90 | 0.38/N.C. | 0.02/0.12 | 0.09/0.43 | 0.06/0.34 |

Percent Infection in Check Plants: 68%

Obviously, many modifications and variations of the invention, described hereinabove and in the claims, can be made without departing from the essence and scope thereof.

What is claimed is:

1. A compound of the formula:

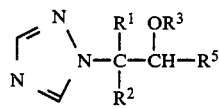

wherein
$R^1$ is isopropoxycarbonyl, t-butoxycarbonyl, or neopentoxycarbonyl;
$R^2$ is hydrogen, methyl or ethyl;
$R^3$ is hydrogen or a compatible cation;
$R^5$ is 2,4-dihalophenyl.

2. The compound of claim 1 wherein $R^3$ is hydrogen and $R^1$ is isopropoxycarbonyl or t-butoxycarbonyl.

3. The compound of claim 1 wherein $R^2$ is hydrogen or methyl.

4. The compound of claim 1 wherein $R^5$ is 2,4-dichlorophenyl.

5. The compound of claim 4 wherein $R^2$ is hydrogen or methyl.

6. The compound of claim 5 wherein $R^1$ is t-butoxycarbonyl.

7. The compound of claim 6 wherein $R^2$ is hydrogen.

8. The compound of claim 7 wherein $R^3$ is hydrogen.

9. The compound of claim 5 wherein $R^1$ is isopropoxycarbonyl.

10. The compound of claim 9 wherein $R^3$ is hydrogen.

11. The compound of claim 5 wherein $R^1$ is neopentoxycarbonyl.

12. The compound of claim 11 wherein $R^3$ is hydrogen.

13. The compound of claim 12 wherein $R^2$ is hydrogen.

14. A method for controlling fungi which comprises contacting said fungi or their growth environment with a fungicidally effective amount of a compound of claim 1.

15. A method for controlling fungi which comprises contacting said fungi or their growth environment with a fungicidally effective amount of the compound of claim 7.

16. A method for controlling fungi which comprises contacting said fungi or their growth environment with a fungicidally effective amount of the compound of claim 13.

17. A fungicidal composition comprising a compatible carrier and a fungicidally effective amount of the compound of claim 1.

18. A fungicidal composition comprising a compatible carrier and a fungicidally effective amount of the compound of claim 7.

19. A fungicidal composition comprising a compatible carrier and a fungicidally effective amount of the compound of claim 13.

20. A method for advantageously altering the growth pattern of plants which comprises contacting the foliage or stems or the growth medium of such plants with a plant growth regulating effective amount of the compound of claim 1.

21. A plant growth composition comprising a plant growth regulating effective amount of the compound of claim 1 and a compatible carrier.

* * * * *